(12) United States Patent
De Lucca et al.

(10) Patent No.: US 8,497,249 B1
(45) Date of Patent: Jul. 30, 2013

(54) **FUNGICIDAL PROPERTIES OF THREE SAPONINS FROM *CAPSICUM FRUTESCENS***

(75) Inventors: Anthony J. De Lucca, Metairie, LA (US); Stephen M. Boue, New Orleans, LA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 665 days.

(21) Appl. No.: 12/572,821

(22) Filed: Oct. 2, 2009

Related U.S. Application Data

(60) Provisional application No. 61/102,123, filed on Oct. 2, 2008.

(51) Int. Cl.
*A01N 43/90* (2006.01)
*A01N 43/08* (2006.01)
*A61K 31/7048* (2006.01)
*A01N 65/38* (2009.01)

(52) U.S. Cl.
USPC ............... 514/26; 536/6; 536/6.1; 536/6.3; 424/760

(58) Field of Classification Search
USPC ........................... 514/26; 424/760
See application file for complete search history.

(56) References Cited

U.S. PATENT DOCUMENTS 6,310,091 B1 * 10/2001 De Lucca et al. ............. 514/462

OTHER PUBLICATIONS

De Lucca et al. Can. J. Microbiol., 2006, 52, p. 336-342.*
FDA Guidance for Industry on Container Closure Systems for Packaging Human Drugs and Biologics, May 1999.*

* cited by examiner

*Primary Examiner* — Shaojia Anna Jiang
*Assistant Examiner* — Jonathan S Lau
(74) *Attorney, Agent, or Firm* — John D. Fado; Evelyn M. Rabin; Gail E. Poulos

(57) ABSTRACT

CAY-1 is a fungicidal saponin from the cayenne pepper (*Capsicum frutescens*) fruit. The saponins 1081 and 919, closely elute with, and are close structural relatives of, CAY-1. Saponin 1081 is poorly antifungal while 919 has no antifungal properties. Nongerminated and germinating conidia of *Aspergilus flavus, A. fumigatus, A. niger, Fusarium oxysporum, F. solani*, and *F. verticilioides* were tested against pure CAY-1 and CAY-1:1081:919 at ratios of 8:1:1, 6:2:2 and 4:3:3 and efficacy was determined after various incubation times. Pure CAY-1 and all saponin mixtures were significantly ($p<0.001$) lethal to the germinating conidia of *A. flavus, A. niger*, and *F. solani*. All saponin mixtures were equal or superior to pure CAY-1 in antifungal properties. Mixtures of the naturally occurring inactive or poorly fungicidal saponins with reduced levels of CAY-1 display superior fungicidal properties when compared to pure CAY-1 at the same dose levels.

13 Claims, 9 Drawing Sheets
(6 of 9 Drawing Sheet(s) Filed in Color)

Effect of CAY-1:1081:919 Mixtures on *Aspergillus flavus* Viability

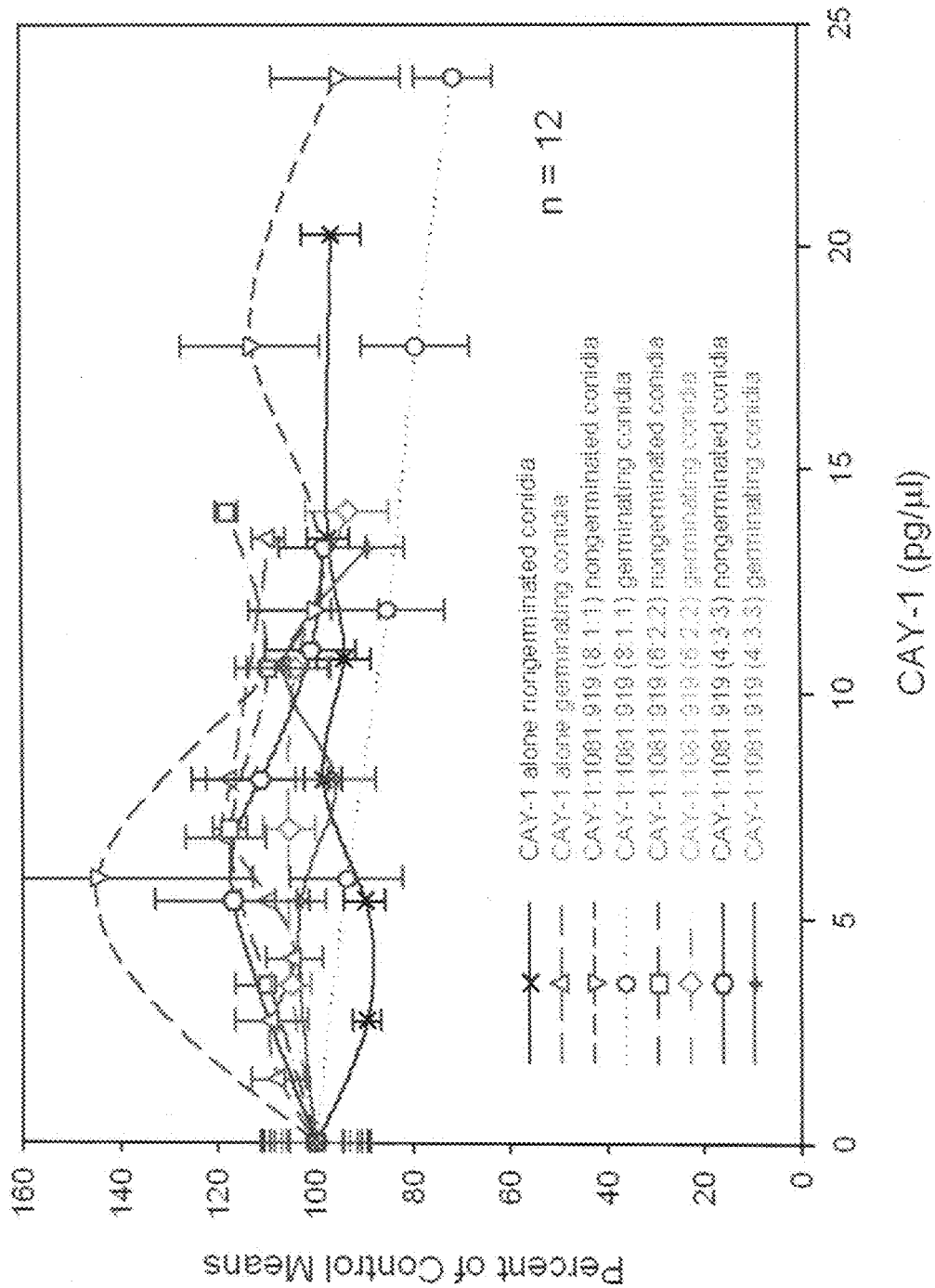

Effect of CAY-1:1081:919 Mixtures on *Aspergillus niger* Viability

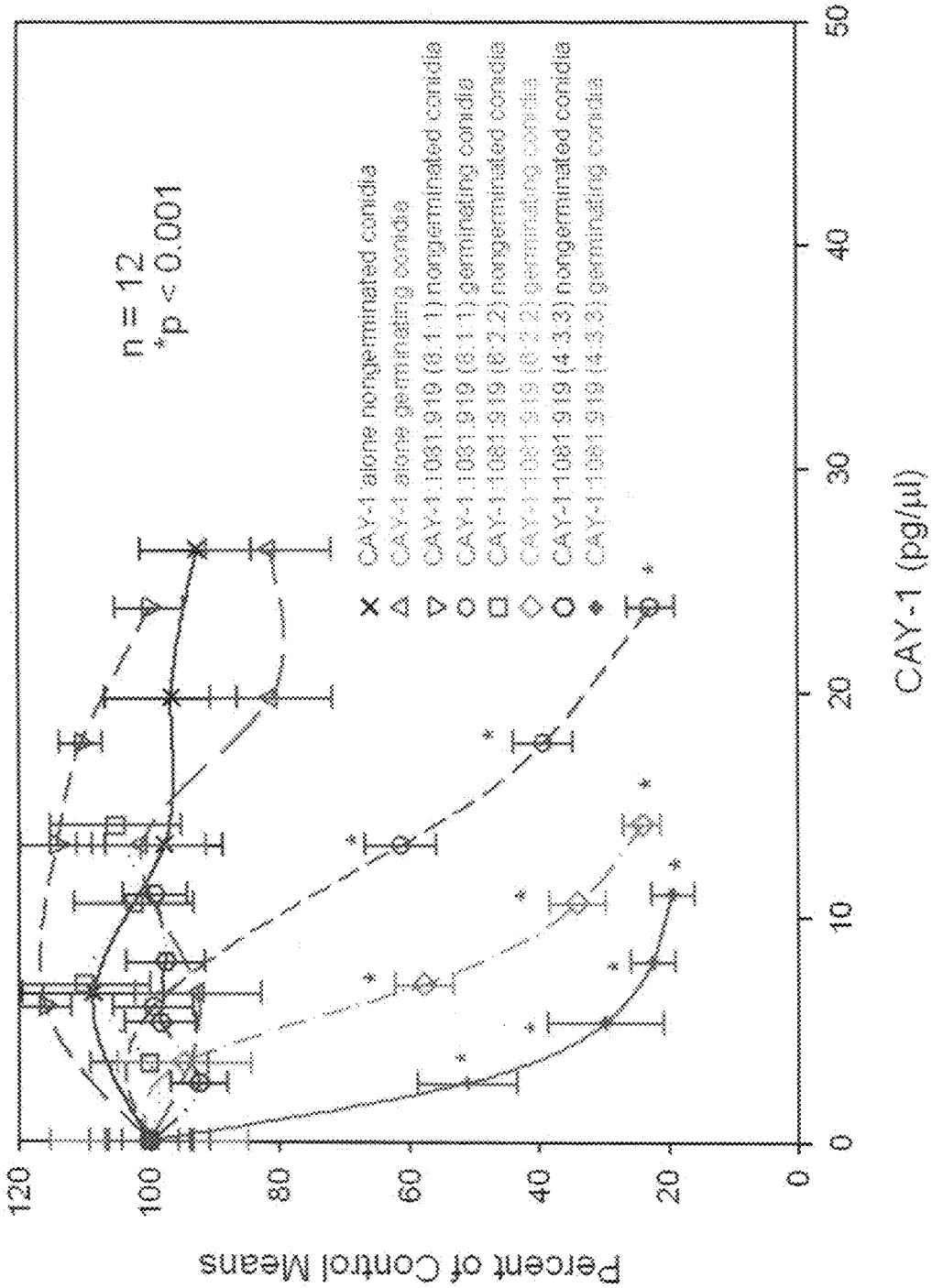

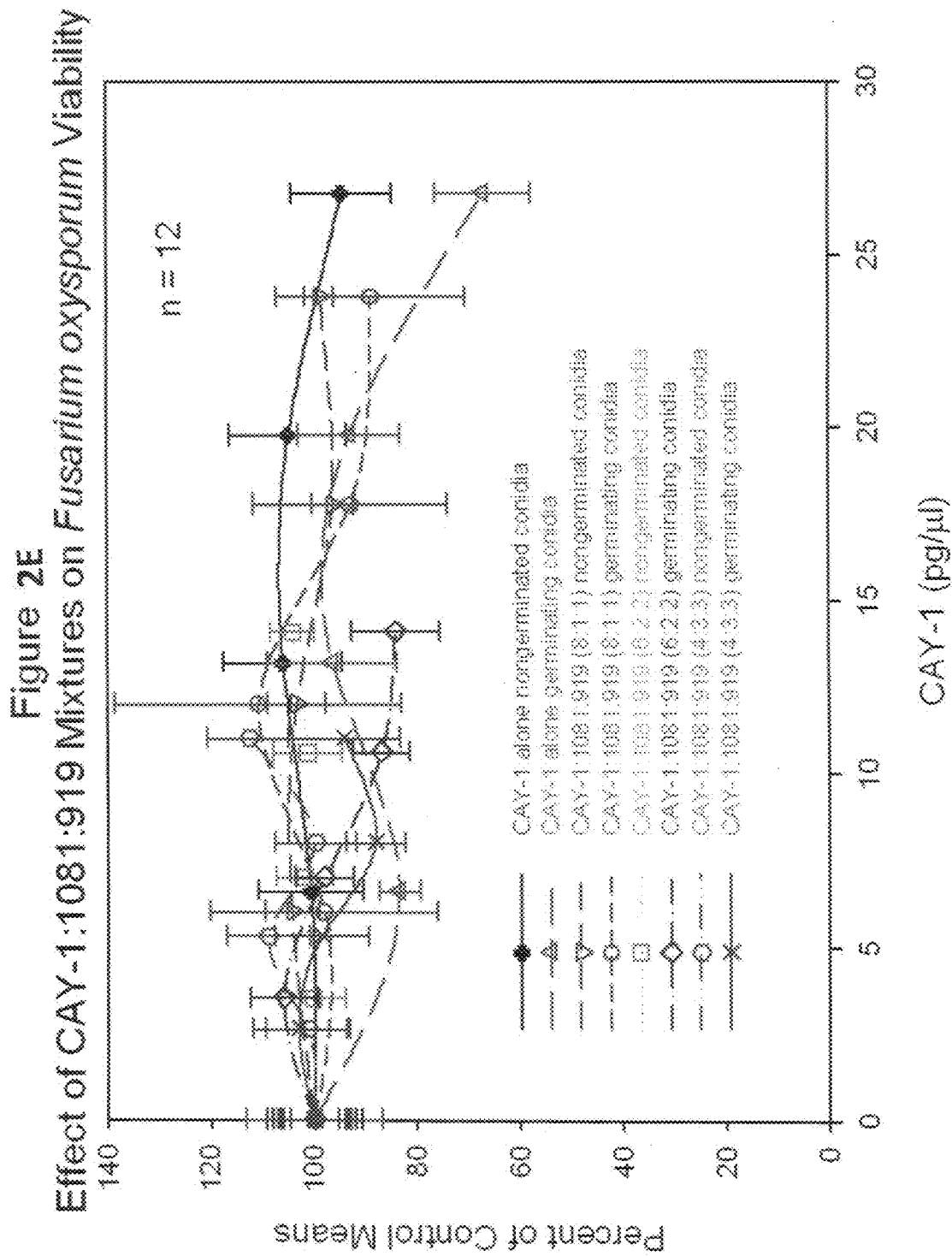

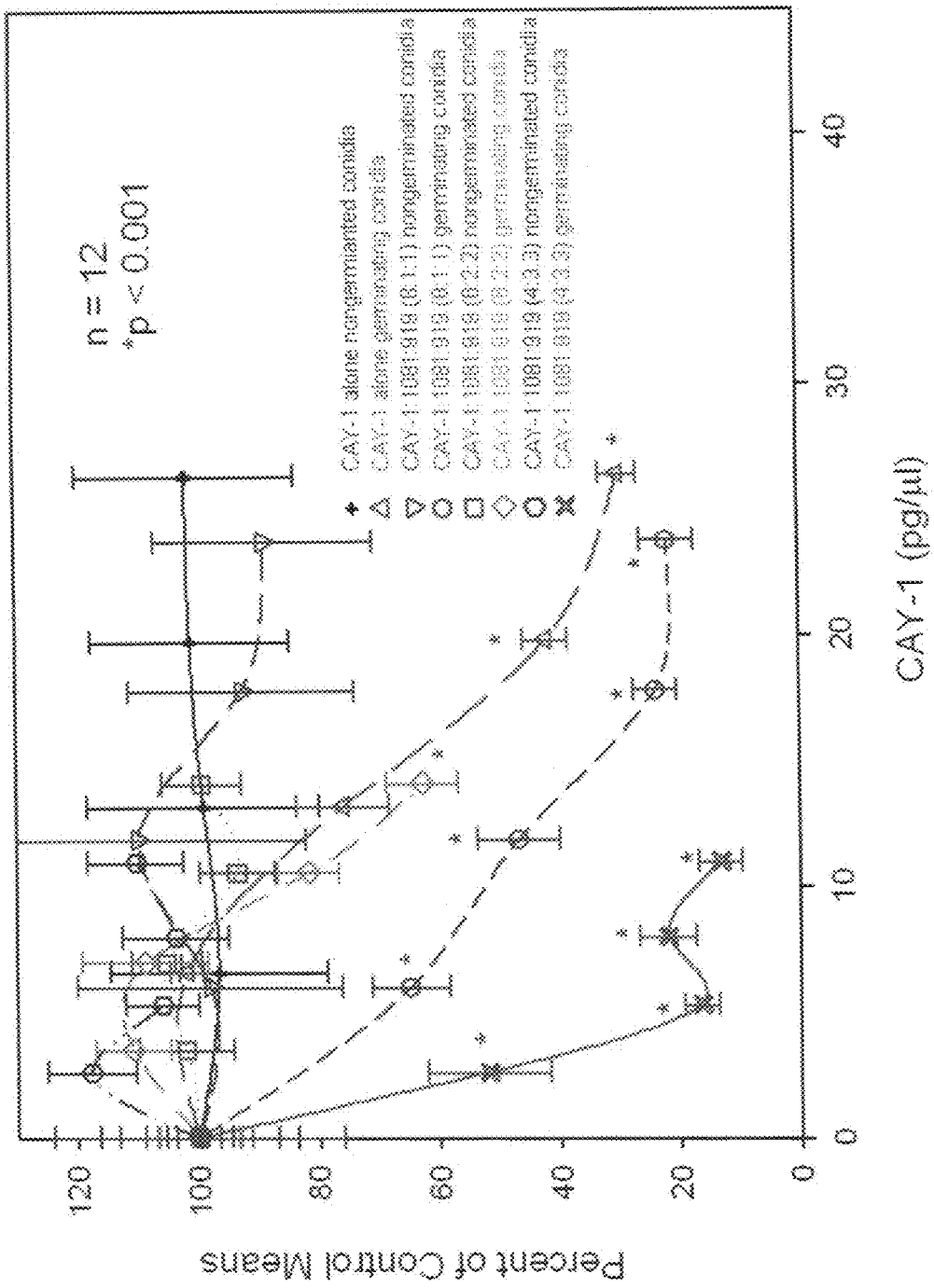

FUNGICIDAL PROPERTIES OF THREE SAPONINS FROM *CAPSICUM FRUTESCENS*

This application claims the benefit of U.S. Provisional Application No. 61/102,123, filed Oct. 2, 2008, which is incorporated herein by reference in its entirety.

BACKGROUND OF THE INVENTION

1. Field of the Invention

This invention relates to fungicidal compositions comprising particular concentrations of three saponins extracted from *Capsicum* spp. The invention further relates to methods for using the antifungal compositions for improving crop resistance to fungi, including aflatoxin-producing fungi, and for treating animals and human patients for fungal-induced conditions and disease.

2. Description of the Relevant Art

Archeological evidence indicates that peppers belonging to the genus *Capsicum* were domestically used by Mesoamerican cultures at least 6100 years ago and predates pottery in some regions (Perry et al. 2007. *Science* 315: 986-988). Historically, these peppers were used by the native peoples of Mesoamerica in food flavoring (Molina-Torres et al. 1999. *J. Ethnopharm.* 64: 241-248). They still constitute an important component of the Mexican diet. In addition to food flavoring, various parts of these plants were also used as medicinal agents by the Mesoamerican peoples. *Capsicum* spp. produce a number of capsaicinoids, with capsaicin being the main capsaicinoid produced by these plants. It stimulates sensory afferent neurons (Buck and Burks. 1986. *Pharm. Rev.* 38:179-226; Caterina et al. 1997. *Nature* 398:816-824). Capsaicin also inhibits bacterial growth and causes platelet aggregation (Caceres et al. 1991. *J. Ethnopharm.* 31:193-208; Molina-Torres, supra; Wang et al. 1984. *Thrombosis Res.* 36:497-507; Sylvester and LaHann. 1989. *Proc. Western Pharm. Soc.* 32:95-100; Hogaboam and Wallace. 1991. *Eur. J. Pharm.* 202:129-131). Capsaicin also causes membrane fluidity changes at concentrations corresponding to antibacterial and anti-platelet concentrations (Tsuchiya, H. 2001. *J. Ethnopharm.* 75:295-299).

*Capsicum* spp. also produce saponins, which are amphiphilic compounds having detergent-like properties and commonly found in plants. In vivo, saponins bind to cholesterol and bile acids and reduce the presence of these compounds in the blood of animals (Cho et al. 2006. *Eur. J. Pharm.* 550:173-179; Li et al. 2008. *Phytotherapy Res.* 22:159-164; Son et al. 2007. *Biosci. Biotech. Biochem.* 71:3063-3071). Much less is known of *Capsicum* spp. saponins than capsaicinoids present in these plants. CAY-1 (FIG. 1), a steroidal saponin present in cayenne pepper and paprika, has potent fungicidal properties against a number of fungi of agricultural and medical importance (De Lucca et al. 2002. *Med. Mycology* 40:131-137; De Lucca et al. 2008. *Am. J. Enol. Viticult.* 59:67-72, Renault et al. 2003. *Med. Mycology* 41:1-7; Stergiopoulou et al. 2008. *Med. Mycology* 46:1-7; Yajima et al. 2000. *Food Sci. Tech. Res.* 6:99-101). CAY-1, in vitro, has shown additive synergy with Amphotericin B and intraconazole against *Aspergillus flavus*, *A. fumigatus* and *A. niger* (De Lucca et al. 2006a. *Chemotherapy* 52:285-287).

However, other *Capsicum* spp. saponins are not as active. For example, the saponins 1081 and 919 (FIG. 1) closely elute with and are close structural relatives of CAY-1; however, saponin 1081 is poorly antifungal, while 919 has no antifungal properties (De Lucca et al. 2006b. Canadian J. Microbiol. 52:336-342). They lack one and two glucose moieties, respectively, present in CAY-1. No additional information concerning these saponins is known. In planta, CAY-1, 1081 and 919, in a weight-to-weight-to weight measurement, exist in a ratio of 4:3:3 (data not published).

While the anti-fungal properties of the saponins CAY-1, 1081, and 919 in pure form are known in the art, there still remains a need in agriculture for effective fungicidal compositions for reducing fungal and aflatoxin contamination of crops and for pharmaceutical anti-fungal compositions for treating animals for fungal-induced diseases and conditions. The present invention, described below, provides potent fungicidal compositions comprising CAY-1 (at suboptimal concentrations) together with 1091 and 919 and methods of using these compositions to effectively reduce fungal contamination of crops and to treat animals and humans having fungal-induced diseases and conditions.

SUMMARY OF THE INVENTION

We have determined that a mixture comprising: (1) a suboptimal concentration of the potent fungicide CAY-1, (2) the weak antifungal saponin 1081 lacking the number 4 glucose moiety of CAY-1, and (3) the saponin 919 having no antifungal activity and lacking the number 3 and 4 glucose moieties of CAY-1, is a potent fungicidal composition.

In accordance with this discovery, it is an object of the invention to provide a fungicidal composition that has fungicidal activity against a large variety, including several genera, of fungal organisms associated with diseases in plants, animals, and humans.

It is particular object of the invention to provide a fungicidal composition that is lethal against *Aspergillus flavus*, *A. niger*, *Fusarium solani*, and *F. verticilioides* (formerly *F. moniliforme*) and other fungi.

It is another object of the invention to provide an antifungal composition for improving crop resistance to fungi, including aflatoxin-producing fungi.

It is still another object of the invention to provide a pharmaceutical composition that acts as a fungicidal agent for treating fungal-induced diseases including dermatological conditions.

It is a further object of the invention to provide a method for inhibiting growth of a fungal organism.

It is an additional object of the invention to provide a method for preventing or minimizing fungal-induced disease in plants and contamination of crops by aflatoxin.

A further object of the present invention is to provide a method for treating animals and humans for fungal-induced disease, including dermatological conditions.

Also part of this invention is a kit, comprising the fungicidal composition comprising: (1) a suboptimal concentration of the potent fungicide CAY-1, (2) the weak antifungal saponin 1081 lacking the number 4 glucose moiety of CAY-1, and (3) the saponin 919 having no antifungal activity and lacking the number 3 and 4 glucose moieties of CAY-1; and instructions for the use of the kit.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIGS. 2A-2F depict the lethality of saponins CAY-1 alone and mixtures of CAY-1, 1081 and 919 for (A) *Aspergillus flavus*, (B) *Aspergillus fumigatus*, (C) *Aspergillus niger*, (D) *Fusarium verticilioides (moniliforme)*, (E) *Fusarium oxysporum* and (F) *Fusarium solani*.

DETAILED: DESCRIPTION OF THE INVENTION

Figure 1:
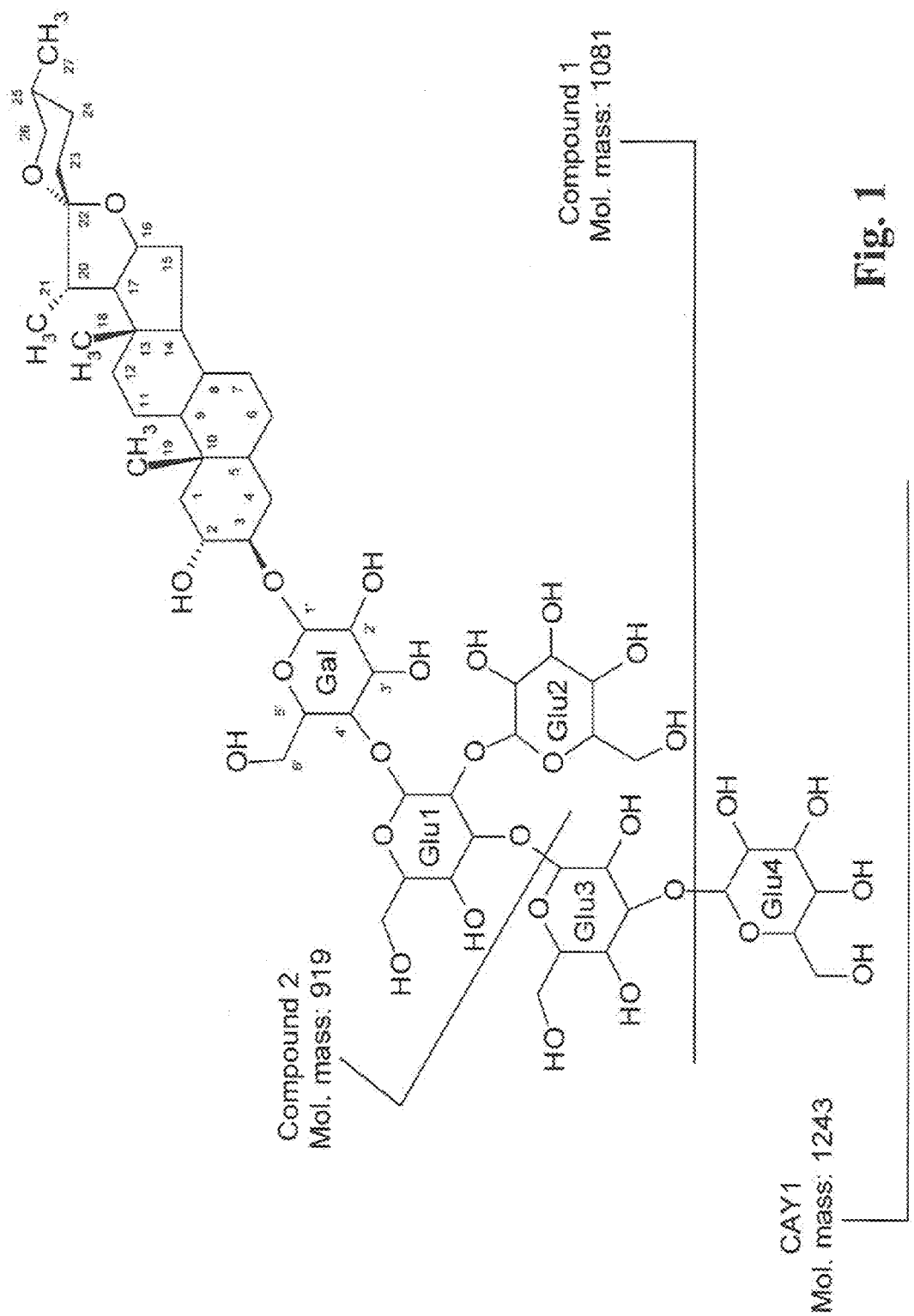
FIG. 1 shows the structures of the cayenne pepper saponins CAY-1, 1081 and 919.

The present invention relates generally to a natural plant product with fungicidal properties that is a composition comprising a mixture of (1) a suboptimal concentration of a potent fungicide CAY-1, (2) the weak antifungal saponin 1081 lacking the number 4 glucose moiety of CAY-1, and (3) the saponin 919 having no antifungal activity and lacking the number 3 and 4 glucose moieties of CAY-1. The composition is useful in agriculture for improving crop resistance to fungi, including aflatoxin-producing fungi. It is also a pharmaceutical composition for treating animals and human patients for fungal-induced diseases and conditions.

Published reports indicated that plant saponins interact with fungal-membrane sterols resulting in the loss of membrane integrity (Keukens et al. 1995. *Biochim. Biophys. Acta* 1240:216-228; Nishikawa et al. 1984. *J. Biochem.* (Tokyo) 96:1231-1239). Electron microscopic studies indicate that pores are formed in the membranes by the saponins (Armah et al. 1999. *Biophysical J.* 76:281-290; Gogelein and Huby. 1984. *Biochim. Biophys. Acta* 773:32-38; Herrera-Arellano et al. 2007. *Planta Medica* 73:1568-1573; Zhang et al. 2006. *J. Ethnopharmacol.* 103:76-84). The sugar chains attached to the sterol are important to the loss of membrane integrity as well as antifungal properties, with loss of these sugar moieties resulting in loss of activity (Armah, supra; De Lucca et al. 2006b, supra; Keukens et al. 1992. Biochim. Biophys. Acta 1110:127-136, Keukens at al. 1995, supra). The cayenne saponins 1081 (weakly antifungal) and 919 (no antifungal properties) have one and two fewer glucose moieties than does CAY-1 (De Lucca et al. 2006b, supra). Loss of antifungal activity observed in saponins 1081 and 919 observed earlier is possibly due to the reduction or disappearance of membrane permeabilizing properties brought about by the loss of sugar residues.

Saponins may also employ another antifungal mode of action. A recent study showed that the saponin α-tomatine was lethal to the fungal pathogen, *Fusarium oxysporum*, by activating phosphotyrosine kinase and monomeric G-protein signaling pathways leading to $Ca^{2+}$ elevation and reactive oxygen species (ROS) burst in the cells (Ito et al. 2007. *FEBS Letters* 581:3217-3222). Intracellular ROS can cause cell death due to the oxidation of biopolymers and destruction of cell membranes and organelles such as mitochondria (Cabiscol et al. 2000. *J. Biol. Chem.* 275:27393-27398; Klyubin et al. 2000. *Membrane Cell Biol.* 13:557-566). The rapid and significant viability loss observed in this study with fungi is similar to that caused by ROS-mediated death in *Escherichia coli* (Maness et al. 1999. *Appl. Environ. Microbiol.* 65:4094-4098). The involvement of a ROS cascade of events in cell death would explain the lack of death observed in the treated nongerminated conidia in this study because they have no ongoing metabolic processes that would initiate the ROS cascade.

The composition of the invention has been tested for its effects on *Aspergillus flavus*, *A. fumigatus*, *A. niger*, *Fusarium oxysproium*, *F. solani*, and *F. verticilioides* (formerly *F. moniliforme*). *A. flavus* is a serious problem in food and feed grains, especially oilseeds such as corn, cotton, and peanut. *A. flavus* produces aflatoxins, toxic secondary metabolites, which are the most potent naturally occurring carcinogens known which can kill humans and animals, especially fowl. *A. fumigatus* causes lethal pulmonary infections of domestic fowl, especially those confined in fowl confinement areas leading to huge economic losses. Horses are susceptible to pulmonary and eye infections by this fungus. Immunocompromised patients can develop pulmonary infections after inhaling this fungus. *A. niger* is generally considered to be a saprophyte in nature; however, it can become a secondary pathogen in grapes. *Fusarium oxysporum* causes wilt in melons. In addition, it causes pulmonary infections in immunocompromised patients. *F. solani* causes sudden death syndrome of soybeans and crown and foot rot in squash. It too is a potential pulmonary pathogen of immunocompromised patients. *F. verticilioides* (formerly known as *F. moniliforme*) is a producer of the mycotoxins group known as the fumonisins. This mycotoxin causes equine leukoencephalomalacia and porcine pulmonary edema. The fumonisins also promote cancer formation.

The fungicidal properties of the composition of the invention are enhanced by reducing the CAY-1 content by as much as 60% in mixtures of the three saponins. Thus, a composition containing a suboptimal concentration of the known potent fungicidal agent CAY-1 and also containing a weak fungicidal agent and a non-fungicidal agent actually had increased antifungal activity. The increased antifungal activity observed in this study was unexpected because the concentration of the only fungicidal saponin, CAY-1, of the three saponins tested in the mixtures was reduced and replaced by the inactive 1081 and 919. It is possible that sub-lethal doses of CAY-1 used in the mixtures caused sufficient membrane perturbations to allow the smaller saponins to pass through the cell membrane and affect the ROS cascade. Additional research will be needed to clarify this mechanism of action.

The composition of this invention comprising the mixture of (1) a suboptimal concentration of the potent fungicide CAY-1, (2) the weak antifungal saponin 1081 lacking the number 4 glucose moiety of CAY-1, and (3) the saponin 919 having no antifungal activity and lacking the number 3 and 4 glucose moieties of CAY-1 will typically be applied in a suitable solid or liquid carrier. The carrier is preferably a physiologically and/or pharmaceutically tolerable (acceptable) carrier or vehicle that is compatible with the organism being treated.

The selected carrier or vehicle would of course be consistent with the intended mode of application or administration of the composition of the invention. The fungicidal composition of the invention and carrier can be applied or administered by any conventional method to the locus of fungal infection or potential fungal infection. For agronomic applications, examples of such loci include, without limitation thereto, surfaces of plant foliage, flowers, seeds, fruits and vegetables, roots, tubers, and even the soil in the vicinity of seeds, plants, and the like. The composition could also be administered to plants systemically, as by injection or absorption into the tissues. Typical modes of application for agronomic uses would include spraying, fogging, atomizing, dusting, broadcasting, coating, drenching, and the like. Compositions of the invention intended for agronomic uses may be formulated as an aqueous spray or dip, wettable powder, drench, dust, granule, pellet, etc. Typical carriers used in such formulations would include without limitation, mineral earths, such as silicas, silica gels, silicates, talc, kaolin, limestone, lime, chalk, bole, loess, clay, dolomite, diatomaceous earth, calcium sulfate, magnesium sulfate, and magnesium oxide; organic materials, such at cereal hulls, shredded tree bark, wood chips, nutshells, and cellulose powders; and fertilizer, such as ammonium sulfate, ammonium phosphate, ammonium nitrate, ureas. The composition of the invention containing the CAY-1, 1081, and 919 saponins may be applied to the aforementioned solid carriers as a surface treatment (e.g. a spray), or may be blended therewith and shaped into granules or pellets. Formulations comprising the CAY-1, 1081, and 919 saponin composition of the invention may also include other adjuvants, such as wetting agents, sticking agents and the like. When used together with a liquid vehicle, the CAY-1, 1081, and 919 saponin composition of the invention could either be dissolved or dispersed therein or blended with other active ingredients, such as herbicides, insecticides, bactericides, nematocides, molluscicides, growth regulators, micronutrients, and the like.

For human and veterinary applications, typical carriers are aqueous carriers such as water, buffered aqueous solutions, aqueous alcoholic mixtures, and the like. Compositions comprising carriers that are for pharmaceutical use, particularly for use in mammals, comprise a carrier that is pharmaceutically-acceptable. Depending on the intended mode of administration, the compounds and compositions of the present invention can be in various pharmaceutical compositions. The compositions will include, as noted above, an effective amount of the selected antifungal composition of the invention in combination with a pharmaceutically acceptable carrier and, in addition, may include other medicinal agents, pharmaceutical agents, carriers, adjuvants, diluents, excipients, etc. By "pharmaceutically acceptable" is meant a material that is not biologically or otherwise undesirable, i.e., the material may be administered to a plant, animal, or human along with the antifungal composition of the invention without causing any undesirable biological effects or interacting in a deleterious manner with any of the other components of the pharmaceutical composition in which it is contained. Examples of such carriers are known in the art and need therefore not be provided herein. For instance, tablets and capsules intended for oral administration may contain binding agents, such as starch, gums, and polyhydroxy alcohols; fillers, such as sucrose, lactose, starch, sorbitol; disintegrants, such as potato starch or sodium starch glycollate; surfactants, such as sodium lauryl sulphate; suspension agents, emulsifiers, preservatives, flavorants, minerals, salts, effervescence agents, etc. For human and veterinary applications, the composition could be administered through various routes, including oral, nasal, rectal, parenteral, implant, topical, and the like. Particular advantage of the antifungal properties of the CAY-1, 1081, and 919 saponin composition of the invention can be taken by incorporating the saponin composition into lotions, ointments, creams, eye, ear and nose drops, shampoos, body powders, pessaries, wound dressings, inhalers, sanitary devices, skin patches, sprays, aerosols, and so forth.

As used herein "in amounts effective", "an amount effective" or "an effective amount" refer to the amount of the antifungal composition of the invention administered wherein the effect of the administration acts to reduce fungal and toxin contamination of agricultural commodities or is effective to obtain a reduction in the level of disease, as measured by fungal growth or the symptoms associated with fungal growth, relative to that occurring in an untreated control under suitable conditions of treatment. In cases where the composition of the invention is applied prophylactically, use of these terms means that the disease is prevented at a significant level relative to untreated controls. It is implied that an effective amount of the CAY-1, 1081, and 919 saponin composition of the invention would be less than any amount that would induce significant detrimental side effects in the organism being treated for the fungal infection. This implication is reinforced by the use of the expression "pharmaceutically effective amount". The actual rate and amount of application will vary depending on the fungal organism being controlled, the point in its growth phase that treatment is commenced, the substrate being treated and other environmental factors. In the bioassays conducted as described in Example 2 below, for example, the CAY-1, 1081, and 919 saponin composition of the invention was shown to be effective in vitro against the germinating conidia of several pathogenic fungi. The composition was effective against *Aspergillus* species at application levels between about 3.0 and 8.0 µg/ml and against *Fusarium* species at application levels between about 6.0 and 25.0 µg/ml at the ratios of the CAY-1, 1081, and 919 saponins shown. The time course study described in Example 2 indicates that the CAY-1, 1081, and 919 saponin composition rapidly reduces fungal viability at a dose dependent rate.

The pharmaceutical compositions of this invention contain a pharmaceutically and/or therapeutically effective amount of the fungicidal composition of the invention. The effective amount of the fungicidal composition and components thereof is an amount sufficient to prevent or treat the adverse effects of a fungal-induced infection, disease and/or condition. The compositions are administered to a plant or crop, animal, or human in an amount effective to elicit an antifungal response, as compared to a control. The particular dose regimen will be dependent upon a plurality of factors, such as the species of plant or crop and/or the species, size, sex and age of the individual (animal or human) being treated, the target fungal species, the severity of infection, the mode of administration, etc. Upon taking these factors into account, actual dose level and regimen could be readily determined by the person of ordinary skill in the art.

EXAMPLES

Having now generally described this invention, the same will be better understood by reference to certain specific examples, which are included herein only to further illustrate the invention and are not intended to limit the scope of the invention as defined by the claims.

Example 1

Preparation of CAY-1, 1081, 919, and Saponin Test Mixtures

The saponins CAY-1, 1081 and 919 were extracted from aqueous extracts of cayenne pepper as described previously (De Lucca et al. 2002, 2006b, supra). Freeze dried crude extracts, (approximately 120 g) were rehydrated with MilliQ water (Millipore, Billerica, Mass.) in a ratio of 1:1. The rehydrated extract was added to a 200 g column of $C_{18}$ (Waters Corp) and eluted with step gradients of methanol (0, 25, 50, 75, and 100%). The saponins elute in the 100% methanol eluate. The saponins were purified using high performance liquid chromatography/mass spectrometry (HPLC/MS).

CAY-1, 1081 and 919 were dissolved separately in acetonitrile:methanol (60:40). They were mixed together to achieve final ratios of 8:1:1, 6:2:2 and 4:3:3 (the naturally occurring ratio in cayenne pepper). The solvents were evaporated under nitrogen in a heated (45° C. ) glass bed. Prior to complete dryness, approximately 1 ml of 0.1% trifluoroacetic acid was added. This solution addition renders the saponins as an easily observed, white material after freeze-drying (48 hours), which facilitates rapid solubilization in the test buffer (PDB). Without the addition of 0.1% trifluoroacetic acid, the freeze-dried saponins tend to coat the glass vial. This coating effect usually requires sonication for solubilization of the saponins in the test buffer.

Example 2

Fungicidal Activity

Bioassays were performed as described earlier (De Lucca et al. 2002, 2006b, supra). The test fungi (*Aspergillus flavus, A. niger, A. fumigatus, Fusarium oxysporum, F. solani,* and *F. verticilioides* (formerly *F. moniliforme*) were grown on potato dextrose agar (Difco, Detroit, Mich.) slants for seven days (30° C.). When needed, conidia were suspended in 1% potato dextrose broth (Difco, Detroit, Mich.), pH 5.2 (PDB). Using a hemocytometer, stock suspension concentrations were determined and final (working) concentrations of $3 \times 10^4$ conidia/ml were prepared. Following preparation of the conidia, a sample of nongerminated conidia was immediately used in the bioassay to determine the effect of the saponins on nongerminated conidia. An additional conidial sample for each fungus was incubated for 8 hr at 30° C. These conidia were used in bioassays to determine activity of the saponins against germinating conidia.

Individual bioassays consisted of conidia (25 µl), PDB, and the appropriate amount of a mixture of CAY-1, 1081 and 919. The CAY-1 control (CAY-1 alone) bioassays measuring the fungicidal response against the same fungi were performed in a similar manner. Final test volumes were 250 µl. Final test concentrations of CAY-1 alone and the individual saponins in the CAY-1:1081:919 mixtures are listed in Table 1. Controls consisted of conidia and PDB medium.

TABLE 1

Saponin contents of CAY-1 control and the CAY-1, 1081 and 919 mixtures tested in the bioassays.

| Sample | Total Weight[1] | Individual saponin contents[1] | | |
|---|---|---|---|---|
| | | CAY-1 | 1081 | 919 |
| CAY-1 control | 4.97 | 4.97 | 0.00 | 0.00 |
| | 6.60 | 6.60 | 0.00 | 0.00 |
| | 13.20 | 13.20 | 0.00 | 0.00 |
| | 20.00 | 20.00 | 0.00 | 0.00 |
| | 26.40 | 26.40 | 0.00 | 0.00 |
| CAY-1:1081:919 (ratio 8:1:1) | 4.46 | 4.00 | 0.23 | 0.23 |
| | 6.62 | 5.30 | 0.66 | 0.66 |
| | 13.24 | 10.59 | 1.33 | 1.33 |
| | 19.85 | 15.88 | 1.99 | 1.99 |
| | 26.47 | 21.18 | 2.65 | 2.65 |
| CAY-1:1081:919 (ratio 6:2:2) | 6.34 | 3.80 | 1.27 | 1.27 |
| | 12.67 | 7.60 | 2.54 | 2.54 |
| | 19.01 | 11.41 | 3.80 | 3.80 |
| | 25.34 | 15.20 | 5.07 | 5.07 |
| CAY-1:1081:919 (ratio 4:3:3) | 2.66 | 1.06 | 0.80 | 0.80 |
| | 3.53 | 1.41 | 1.06 | 1.06 |
| | 6.64 | 2.66 | 1.99 | 1.99 |
| | 7.95 | 3.18 | 2.39 | 2.39 |
| | 13.28 | 5.31 | 3.99 | 3.99 |
| | 19.84 | 7.94 | 5.95 | 5.95 |
| | 26.56 | 10.56 | 8.00 | 8.00 |

[1]µg/ml

After a 30 min incubation period (30° C.), aliquots (50 µl) of each sample were spread on each of four potato dextrose agar plates. The plates were incubated for 48 hours at 30° C., followed by colony enumeration. Three separate runs per conidial type and fungus were performed (n=12).

Time of fungicidal activity for the saponin mixtures was determined by using the germinating conidia of *A. flavus*. The aforementioned experimental protocol was employed with aliquots tested at 0, 5, 10, 15, 20, 25 and 30 minutes after incubation commenced. Three separate runs were performed (n=12).

Statistical analyses were performed on the data using SigmaStat 3.1 (Systat, Point Richmond, Calif.). Significance (p<0.001) was determined between viability control and test saponin data.

Earlier reports indicated CAY-1 had fungicidal properties against a wide range of fungal genera (De Lucca et al. 2002, supra; Renault, supra). However, 1081 and 919, which closely elute with CAY-1 and are structurally similar to CAY-1 (FIG. 1) do not share its antifungal properties (De Lucca et al., 2006b). Therefore, it was expected that mixtures of these three saponins would result in the loss of fungicidal properties due to the reduction of CAY-1 content per unit weight of sample. However, results indicated that all mixtures of the cayenne saponins were more active than CAY-1 alone for the germinating conidia tested.

Figure 2A:
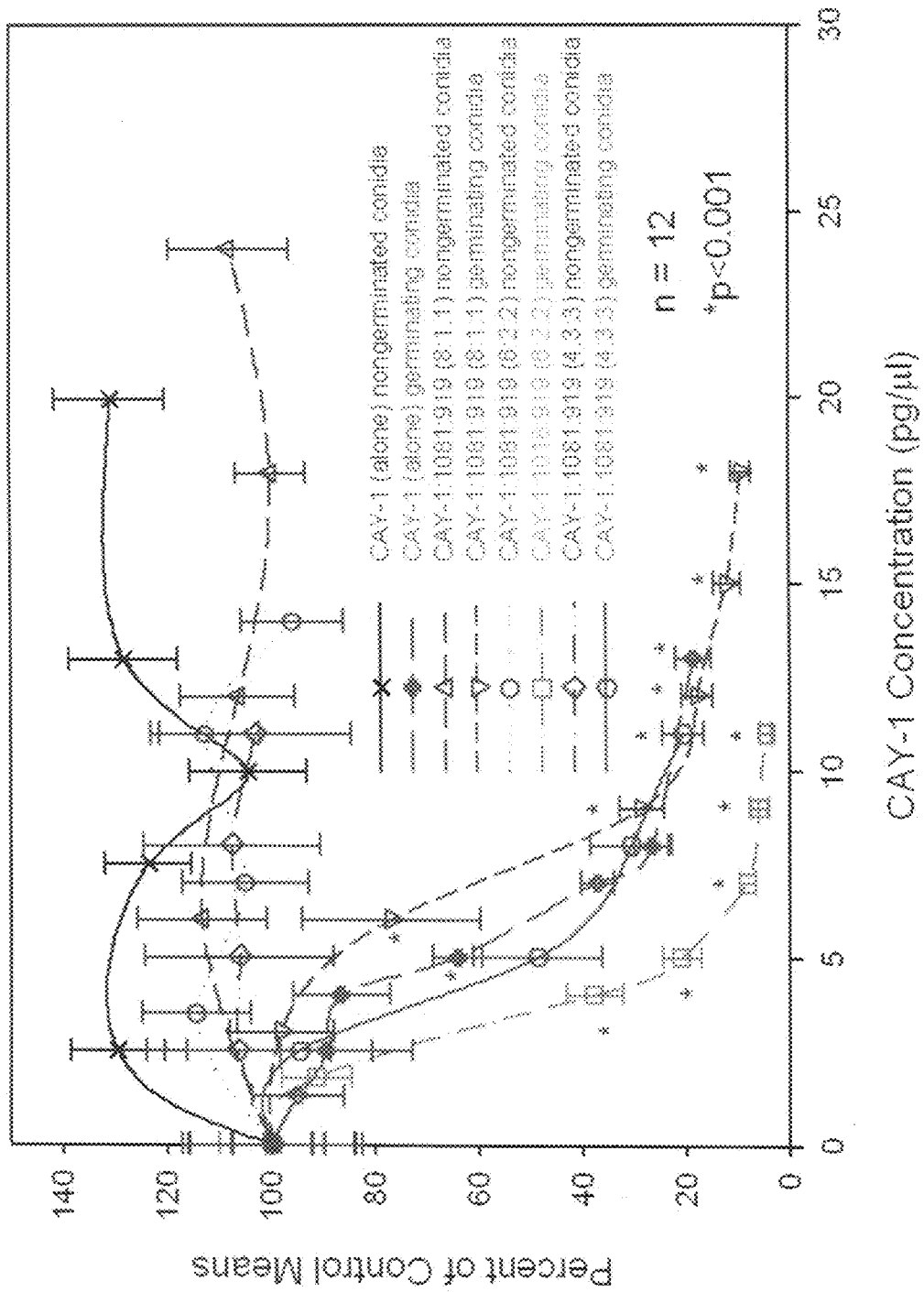
Figure 2C:
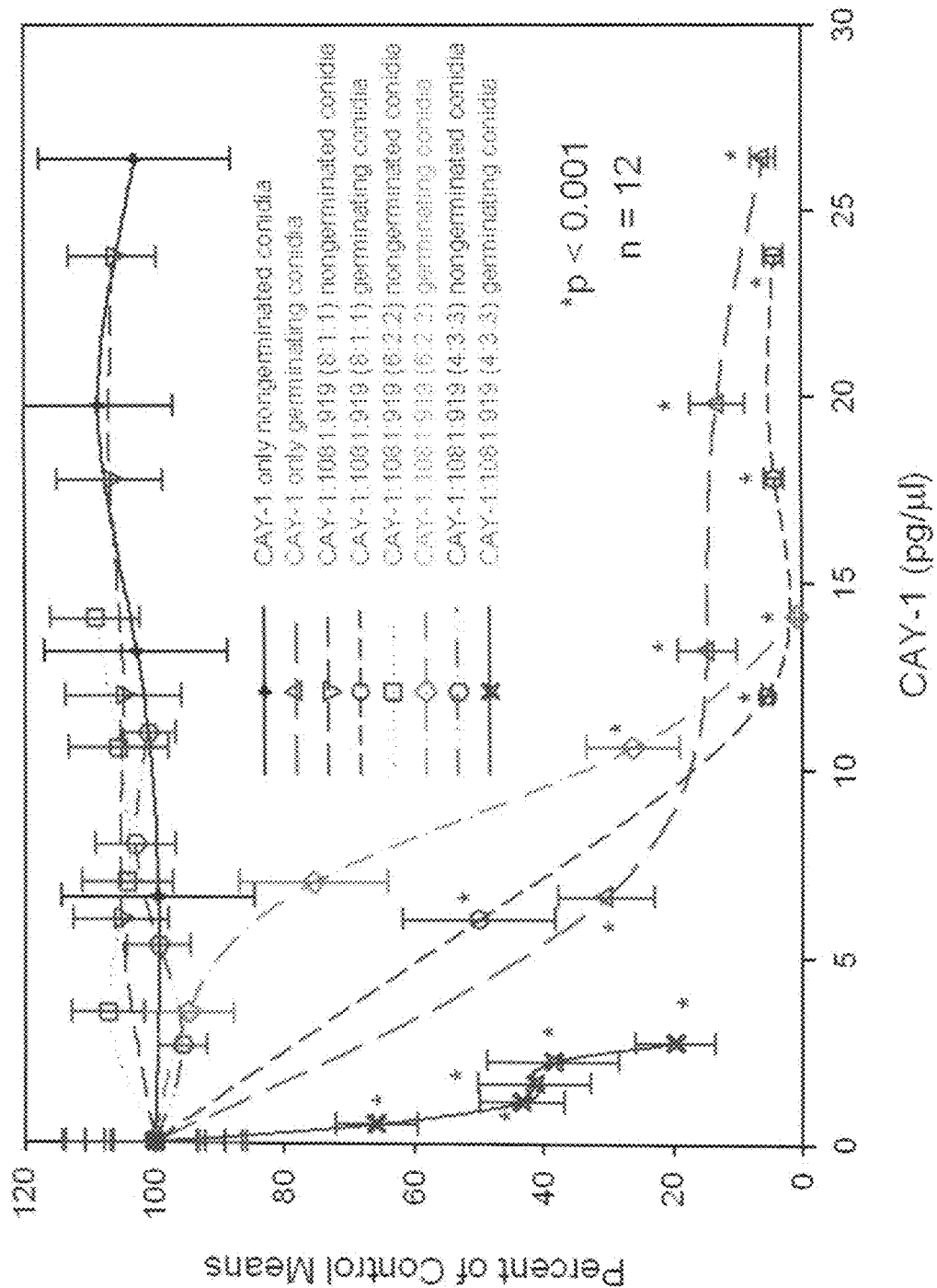

The germinating conidia of *A. flavus* and *A. niger* (FIGS. 2A and 2C), treated with the CAY-1 control and the saponin mixtures, had significantly (p<0.001) lower viability counts than that of the conidial viability controls. The 6:2:2 saponin ratio reduced the viability of the germinating conidia of *A. flavus* (FIG. 2A) by as much as two-fold when compared with the CAY-1 alone and the other saponin mixtures. The viability of germinating conidia of *A. niger* (FIG. 2C) was most reduced by the 4:3:3 saponin ratio which was also found to be significantly (p<0.001) more active than pure CAY-1 and the other saponin mixtures against these conidia. No major differences were observed between the viability reductions observed between the CAY-1, 8:1:1 and 6:3:3 ratio samples. Graphs (FIGS. 2A-F and 3A-D) representing the fungicidal activity of CAY-1 alone and the three mixture ratios of CAY-1, 1081 and 919 used the amount of CAY-1 in the respective samples as a means to compare the fungicidal properties of the samples. CAY-1 was used to "normalize" the data based on the sole saponin (CAY-1) of this test group previously shown (De Lucca et al. 2002, supra) to be fungicidal.

None of the saponin samples were active against the nongerminated and germinating conidia of *A. fumigatus* (FIG. 2B) or the nongerminated conidia of *A. flavus* or *A. niger*.

All saponin mixture samples significantly reduced the viability of the germinating conidia of *F. verticilioides* (formerly *F. moniliforme*) and *F. solani* (FIG. 2D) when compared to the viability control. The CAY-1 sample was inactive against *F. verticilioides* though the mixed saponins significantly reduced germinating conidial viability of this fungus. The 4:33 ratio was again more active than the other saponin mixtures.

CAY-1 was significantly fungicidal against the germinating conidia of *F. solani* (FIG. 2F). When compared by the amount of CAY-1 in each sample, the 4:3:3 ratio sample consistently produced lower viability counts than the other samples. This sample was up to two-fold more active in reducing conidial viability of *F. solani* than the pure CAY-1, 8:1:1 and 6:2:2 ratio samples which have two and one-and-one-half fold more CAY-1, respectively, than the 4:3:3 sample.

Statistical analyses showed that significant differences existed between the three saponin mixtures in their ability to reduce conidial viability of *F. solani* The 4:3:3 saponin mixture produced significantly lower viability counts than CAY-1 alone and the other saponin mixtures. The viabilities of the nongerminated conidia of the tested *Fusarium* isolates were not reduced by CAY-1 alone and the saponin mixtures samples. The viability of the nongerminated and germinating conidia of *F. oxysporum* were not reduced by the test samples.

Results of the viability assays indicate that the CAY-1 controls and the mixtures of the three saponins provide significant viability loss of the germinating, but not the nongerminated, conidia of *A. flavus, A. niger* and *F. solani*. Alone, CAY-1 was inactive against the germinating conidia of *F. verticilioides*. However, the mixtures of the three saponins significantly reduce the viability of *F. verticilioides*.

Table 2 shows the least amount of CAY-1 alone and saponin mixtures (both the total weights as well as CAY-1 portion of each mixture) required for significant viability reduction. The 4:3:3 ratio sample, which contained the least amount of the fungicidal CAY-1, nevertheless produced significant viability loss in the aforementioned germinating conidia. The mixtures reduced the amount of CAY-1 required for activity by as much as 79 percent, depending on saponin mixture and fungal species.

Figure 3A:
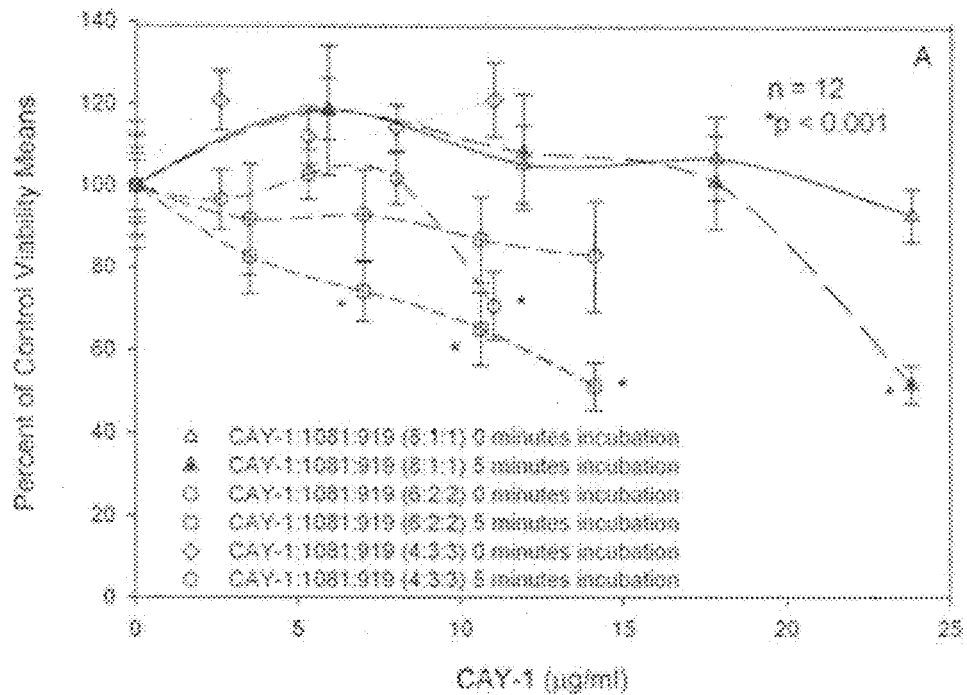
FIGS. 3A-3D show the time course study of CAY-1:1081: 919 mixtures after (A) 0 and 5 minutes, (B) 10 and 15 minutes, (C) 20 and 25 minutes and (D) 30 minutes of incubation. Test fungus: germinating conidia of *Aspergillus flavus*.
Figure 3B:
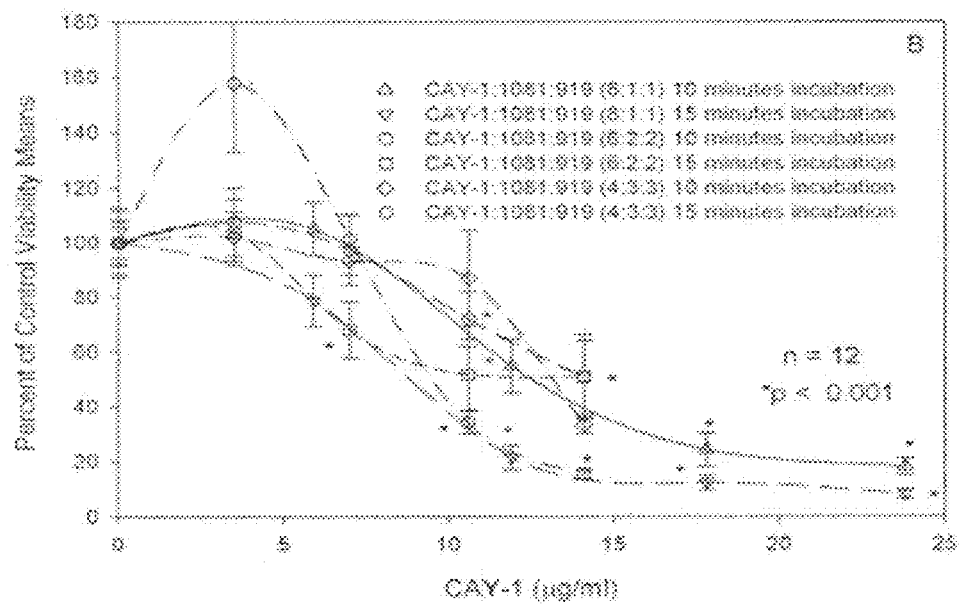
Figure 3C:
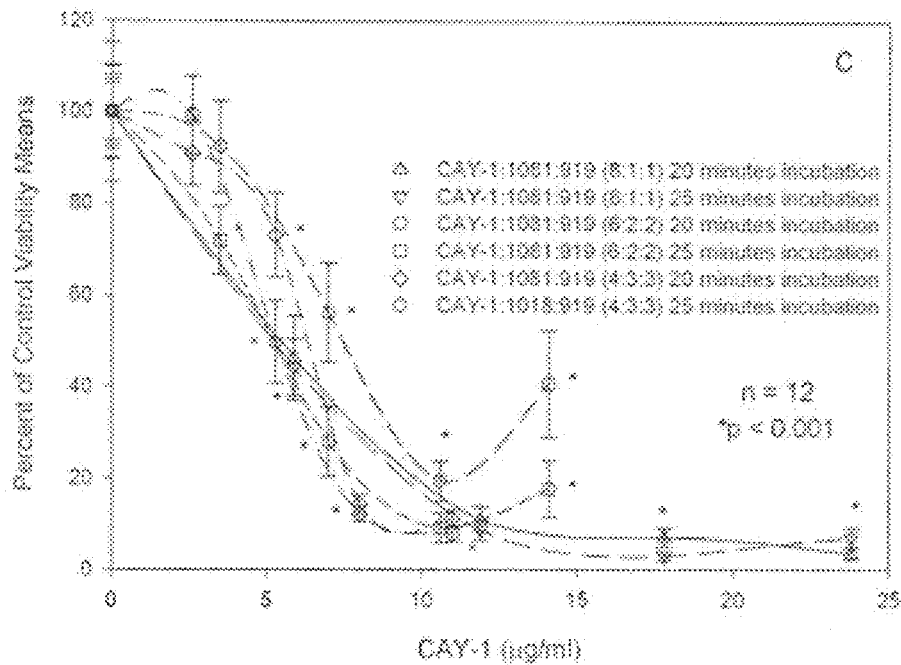
Figure 3D:
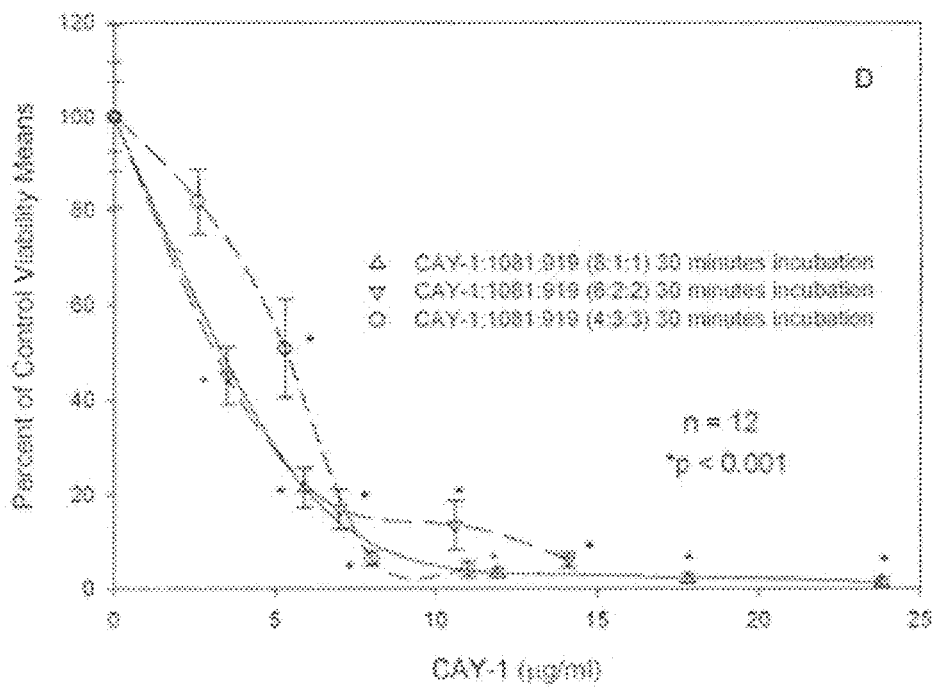

FIG. 3C presents the viability reduction observed at 20 and 25 minutes after incubation began. Significant lethality began at lower dosages than in the shorter time assays as noted in FIGS. 3A and 3B. After 20 minutes of incubation, significant lethality was observed for ratios of 8:1:1, 6:2:2 and 4:3:3 beginning at 6.0, 3.5 and 7.9 µg/ml, respectively. Five minutes later, (25 minutes after incubation began), significant lethality for the saponin mixtures of 8:1:1, 6:22 and 4:3:3 was observed at 6.0, 3.5 and 5.3 µg/ml, respectively. At 30 minutes of incubation (FIG. 3D) significant lethality was observed for all the mixtures beginning at 3.5 µg/ml (6:2:2 ratio), 6.0 (8:1:1 ratio) and 5.3 (4:3:3 ratio).

Time of fungicidal activity data indicate that the mixtures of the fungicide CAY-1 and the saponins 1081 and 919, which have little or no fungicidal properties, can rapidly produce fungicidal activity greater than that of an equal dose of CAY-1 alone against the geminating conidia of *A. flavus*. The CAY-1:1081:919 mixture ratio of 6:2:2 (containing 7.0 µg/ml of CAY-1) caused significant viability loss within five minutes after the start of incubation. In this same time, CAY-1 alone produced significant lethality to germinating *A. flavus* conidia

TABLE 2

Lowest CAY-1 concentrations in test samples, showing Significant (p < 0.001) viability.

| | | | CAY-1 - 1:1081:919 Mixtures | | | | | |
|---|---|---|---|---|---|---|---|---|
| | | | 8:1:1 | | 6:2:2 | | 4:3:3 | |
| Fungus | Conidia Type | CAY-1 Control µg/ml | Total Weight µg/ml | CAY-1 Portion µg/ml | Total Weight µg/ml | CAY-1 Portion µg/ml | Total Weight µg/ml | CAY-1 Portion µg/ml |
| *Aspergillus flavus* | Nongerminated | —# | | | | | | |
| | Germinating | 4.97 | 6.62 | 5.30 | 6.34 | 3.80(23)* | 7.95 | 3.18(36) |
| *A. fumigatus* | Nongerminated | — | — | — | — | — | — | — |
| | Germinating | — | — | — | — | — | — | — |
| *A. niger* | Nongerminated | — | — | — | — | — | — | — |
| | Germinating | 6.62 | 4.46 | 4.00(40) | 6.34 | 3.80(43) | 3.53 | 1.41(79) |
| *Fusarium oxysporum* | Nongerminated | — | — | — | — | — | — | — |
| | Germinating | — | — | — | — | — | — | — |
| *F. solani* | Nongerminated | — | — | — | — | — | — | — |
| | Germinating | 12.43 | 6.62 | 5.30(57) | 25.34 | 15.20 | 6.64 | 2.66(79) |
| *F. verticilioides* | Nongerminated | — | — | — | — | — | — | — |
| | Germinating | — | 13.24 | 10.59 | 12.67 | 7.60 | 6.64 | 2.66 |

No viability reduction observed

CAY-1 alone rapidly reduced the viability of conidia (De Lucca et al. 2002, supra). Here, CAY-1, 1081 and 919 mixtures showed rapid and significant loss of germinating conidial viability. Compared to the control, the loss of germinating *A. flavus* conidial viability by the saponin mixtures begins after 5 minutes of incubation using the saponin ratio of 6:2:2 (FIG. 3A). The total weight of this saponin mixture first showing significant viability reduction was 12.67 µg/ml, with a CAY-1 content of 7.04 µg/ml. The same weight of pure CAY-1 (12.67 µg/ml) was inactive. This was also true for ratio 8:1:1 (total weight: 12.67 µg/ml; CAY-1 content: 11.9 µg/ml) and 4:3:3 (total weight: 12.64 µg/ml; CAY-1 content: 5.3 µg/ml). After 10 minutes, all ratios (8:1:1; 6:2:2, and 4:3:3) of CAY-1, 1081 and 919 produced significantly lower viabilities (FIG. 3B). However, a greater amount of CAY-1 was required in the 8:1:1 (CAY-1 concentration: 13.2 µg/ml) and 4:3:3 (CAY-1 concentration: 26:6 µg/ml) saponin mixtures to achieve significant viability reduction after 10 minutes of incubation than with the 6:2:2 (CAY-1 content: 12:67 µg/ml) saponin ratio mixture. The amount of the saponin mixtures required for significant viability loss after 15 minutes decreased (8:1:1, 19.9 µg/ml; 6:2:2, 6.6 µg/ml and 4:3:3, 13.3 µg/ml).

within five minutes of the initiation of incubation at a dose of 12.4 µg/ml (De Lucca et al., 2002). So, in the presence of the inactive saponins 1081 and 919 in a ratio of 6:2:2 (CAY-1: 1081:919) the amount of CAY-1 required for significant viability loss within five minutes of mixing is reduced by 44 percent. Similar reductions were observed with the other mixtures.

The compositions of the invention comprising a mixture of (1) a suboptimal concentration of a potent fungicide CAY-1, (2) the weak antifungal saponin 1081 lacking the number 4 glucose moiety of CAY-1, and (3) the saponin 919 having no antifungal activity and lacking the number 3 and 4 glucose moieties of CAY-1 were significantly (p<0.001) lethal to the germinating conidia of *A. flavus, A. niger*, and *F. solani* and *F. verticilioides*. The compositions of the invention comprising reduced levels of CAY-1 display superior fungicidal properties when compared to pure CAY-1 at the same dose levels.

All publications and patents mentioned in this specification are herein incorporated by reference to the same extent as if each individual publication or patent was specifically and individually indicated to be incorporated by reference.

The foregoing description and certain representative embodiments and details of the invention have been presented

We claim:

1. An antifungal composition consisting of a mixture consisting of: (1) HPLC/MS-isolated, purified CAY-1 (2) HPLC/MS-isolated, purified saponin 1081 lacking the number 4 glucose moiety of CAY-1 and (3) HPLC/MS-isolated, purified saponin 919 lacking both the number 3 and number 4 glucose moieties of CAY-1 recombined into said mixture, and a carrier or vehicle, wherein amounts of said CAY-1, said saponin 1081 and said saponin 919 in said mixture are present in a ratio of 8:1:1, 6:2:2 or 4:3:3 and wherein the concentration of said CAY-1 in said mixture is reduced by an amount of about 36% to 79% of that concentration of pure CAY-1 which when used alone is required for significant loss of fungal viability, and said composition is effective to significantly inhibit the growth of a fungal organism.

2. The composition of claim 1 wherein the fungal organism is *Aspergillus flavus, A. niger, Fusarium solani*, or *F. verticilioides* (formerly F. moniliforme).

3. A kit, comprising the antifungal composition consisting of a mixture consisting of: (1) HPLC/MS-isolated, purified CAY-1 (2) HPLC/MS-isolated, purified saponin 1081 lacking the number 4 glucose moiety of CAY-1 and (3) HPLC/MS-isolated, purified saponin 919 lacking both the number 3 and number 4 glucose moieties of CAY-1 recombined into said mixture, and a carrier or vehicle, wherein amounts of said CAY-1, said saponin 1081 and said saponin 919 in said mixture are present in a ratio of 8:1:1, 6:2:2 or 4:3:3 and wherein the concentration of said CAY-1 in said mixture is reduced by an amount of about 36% to 79% of that concentration of pure CAY-1 which when used alone is required for significant loss of fungal viability, and said composition is effective to significantly inhibit the growth of a fungal organism; and instructions for the use of the kit.

4. A method for inhibiting the growth of a fungal organism comprising the step of applying to a substrate susceptible to inoculation with said fungal organism the antifungal composition of claim 1 in an amount effective to inhibit said growth.

5. The method of claim 4, wherein said fungal organism is a filamentous fungus.

6. The method of claim 4, wherein said fungal organism is an aflatoxin-producing organism.

7. The method of claim 4, wherein said fungal organism is selected from the group consisting of *Aspergillus flavus, A. niger, Fusarium solani*, and *F. verticilioides* (formerly *F. moniliforme*).

8. The method of claim 4, wherein said substrate is a plant or plant part.

9. The method of claim 4, wherein said substrate is a food or feed material.

10. The method of claim 4, wherein said substrate is a seed.

11. The method of claim 4, wherein said fungal organism is a mycosis-inducing fungal pathogen.

12. The method of claim 11, wherein said substrate is a human or animal.

13. A method for minimizing fungal-induced disease in plants comprising the step of applying to a plant the antifungal composition of claim 1 in an amount effective to minimize said fungal-induced disease.

* * * * *